United States Patent [19]

Beyer

[11] Plant 4,170

[45] Dec. 27, 1977

[54] PEACH TREE-MUTATION OF LORING VARIETY

[75] Inventor: Frederick Beyer, Puducah, Ky.

[73] Assignee: Stark Brothers Nurseries & Orchards Company, Louisiana, Mo.

[21] Appl. No.: 747,683

[22] Filed: Dec. 6, 1976

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Burns, Doane, Swecker & Mathis

[57] ABSTRACT

A new and distinct peach tree variety which originated as a bud mutation of the Loring Peach variety (unpatented) is provided. The fruit of the variety ripens approximately 10 to 14 days earlier than that of the Loring Peach variety, and develops a more intense red color over nearly all of its surface well before the date the fruit softens.

1 Drawing Figure

SUMMARY OF THE INVENTION

The new and distinct variety of peach tree originated in 1965 as a bud mutation of the Loring Peach variety in my orchard maintained on cultivated property in McCracken County, Ky. fronting on Olivet Church Road and lying between the P. & I. Railroad and the I. C. Railroad.

The fruit of the variety is of excellent quality and is substantially identical to that of the Loring Peach variety (unpatented) in size, texture and flavor. However, the fruit ripens approximately 10 to 14 days earlier than that of the Loring Peach variety and develops a much more intense red blush over nearly all of its surface (e.g. 80 percent of its surface) approximately 8 to 10 days prior to harvest maturity. Accordingly, the color of the fruit of the new variety is considered to be more attractive than that of the Loring Peach variety.

Because of the distinctive characteristics of the new variety the plant was asexually reproduced by budding. This propagation shows that the unique combination of characteristics comes true to form and is established and transmitted in succeeding propagation. The specimens described herein were grown and observed near Louisiana, Mo.

BRIEF DESCRIPTION OF THE DRAWING

The accompanying drawing shows typical specimens of the fruit and foliage of my new variety as depicted in color as nearly true as it is reasonably possible to make the same in a color illustration of this character.

DETAILED DESCRIPTION OF NEW VARIETY

Dates of first and last pickings: July 14, 1976 and July 22, 1976 respectively.

Tree: Large size; vigorous; open; upright spreading; hardy; productive.

*Trunk.*—Medium stocky.

*Branches.*—Medium stocky; smooth; glossy. Color — Brown — vinaceous — Russet Plate XXVIII Color Number 7″ — Ridgway's Color Standards. Lenticels — Numerous; small.

*Leaves.*—Large; oval; acutely pointed; medium thin; smooth. Length — 7½ inches. Width — 1¾ inches. Color — Dark Green — Spinach Green Plate V Color No. 29, Tone m. Ridgway's Color Standards. Margin — Glandular; finely serrate. Petiole — Medium short. Glands. — Average number: 2; some opposite, some alternate; medium small; globose; free; not pubescent.

Flowers:

*Dates of first and full bloom.*—Mar. 23, 1976 and Mar. 27, 1976 respectively; medium early.

*Size.*—Large.

*Color.*—Pink — Showy bloom Munsell Hue 2.5R.

Fruit:

*Maturity when described.*—Eating; Date — July 14, 1976; Pike County, Mo.

*Size.*—Uniform; medium large. Axial diameter — 2½ inches. Diameter at right angles to suture planes — 2⅝ inches.

*Form.*—Uniform; unsymmetrical; globose; compressed — toward suture; sides unequal.

*Suture.*—Shallow; extends from base to beyond apex.

*Ventral surface.*—Rounded: slightly lipped; Apex: throughout one left side.

*Cavity.*—Abrupt; elongated in suture plane with suture showing on both sides. Depth — 7/16 inch. Breadth — ⅝ inch.

*Base.*—Rounded.

*Apex.*—Depressed; pistil point, apical.

*Stem.*—Adherence to stone; medium weak.

*Skin.*—Medium thick; medium tough; astringent; tenacious to flesh; no tendency to break. Color — Highly blushed red — Munsell Hue 7/5 RP 3/9. Down—Abundant; medium long; does not roll up when rubbed.

*Flesh.*—Color — Yellow — Munsell Hue 5Y 8/12; mottled with red throughout.

*Surface of pit cavity.*—Color — Pink — Munsell Hue 7.5 RP.

*Amygdalin.*—Wanting; juice moderate rich.

*Texture.*—Firm.

*Fibers.*—Few; tender.

*Ripens.*—Fairly even.

*Flavor.*—Mild.

*Aroma.*—Distinct.

*Eating quality.*—Good.

Stone: Free.

*Fibers.*—Retains short fiber like threads along ridges.

*Size.*—Medium large. Length — 1½ inch. Thickness — ¾ inch.

*Form.*—Oval; cunate toward base.
*Base.*—Oblique; hilum; narrow; oval.
*Apex.*—Acute.
*Sides.*—Equal; curved on right and left side.
*Surface.*—Irregularly furrowed near base; pitted throughout.
*Ridges.*—Rounded toward apex.
*Pits.*—Circular.
*Ventral edge.*—Thick with wing toward base.
*Dorsal edge.*—Narrow; with deep groove throughout; ridges on either side; interrupted.

Use: Market, dessert, canning.
Keeping quality: Good.
Shipping quality: Good.

General notes: Resembles Loring but ripens 10 to 14 days earlier and has deeper red blush over nearly all of surface. Quality is excellent. Color develops 8 or 10 days before fruit softens.

I claim:

1. A new and distinct variety of peach tree, substantially as illustrated and described, which bears fruit of excellent quality which ripens approximately 10 to 14 days earlier than the fruit of the Loring Peach variety (unpatented), and develops a more intense red blush over nearly all of its surface approximately 8 to 10 days prior to harvest maturity.

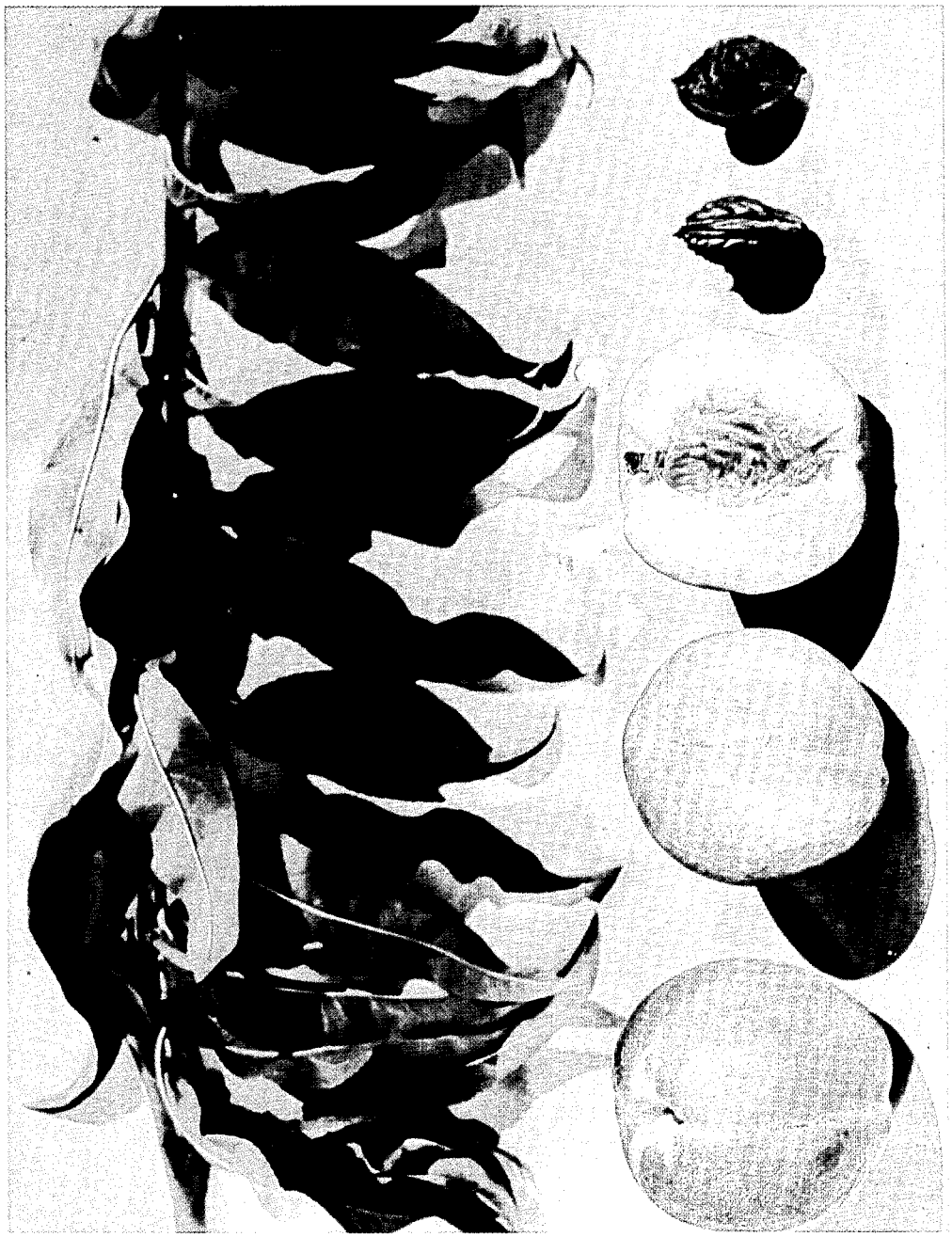

* * * * *